United States Patent
Sankaran et al.

(10) Patent No.: US 10,513,569 B2
(45) Date of Patent: Dec. 24, 2019

(54) BRIDGED METALLOCENE COMPLEX FOR OLEFIN POLYMERIZATION

(71) Applicants: SAUDI BASIC INDUSTRIES CORPORATION, Riyadh (SA); SABIC GLOBAL TECHNOLOGIES B.V., Bergen op Zoom (NL)

(72) Inventors: Nedumbamana Sankaran, Bangalore (IN); Prashant Shinge, Bangalore (IN); Sharankumar Shetty, Bangalore (IN); Girish Chandra, Bangalore (IN); Haif Al-Shammari, Riyadh (SA); Abdulaziz Hamad Al-Humydi, Riyadh (SA); Edward Joseph Nesakumar, Bangalore (IN); Pradeep Jeevaji Nadkarni, Bangalore (IN)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/788,140

(22) Filed: Oct. 19, 2017

(65) Prior Publication Data

US 2018/0044450 A1    Feb. 15, 2018

Related U.S. Application Data

(63) Continuation of application No. 14/912,631, filed as application No. PCT/EP2014/068353 on Aug. 29, 2014, now Pat. No. 9,815,917.

(60) Provisional application No. 61/929,650, filed on Jan. 21, 2014.

(30) Foreign Application Priority Data

Aug. 30, 2013    (EP) ..................... 13182308

(51) Int. Cl.
| | | |
|---|---|---|
| *C08F 110/02* | (2006.01) | |
| *C08F 210/16* | (2006.01) | |
| *C08F 4/6592* | (2006.01) | |
| *C07F 17/00* | (2006.01) | |
| *C07F 7/00* | (2006.01) | |
| *C08F 4/659* | (2006.01) | |

(52) U.S. Cl.
CPC .............. *C08F 110/02* (2013.01); *C07F 7/00* (2013.01); *C07F 17/00* (2013.01); *C08F 4/65927* (2013.01); *C08F 210/16* (2013.01); *C08F 4/65912* (2013.01); *C08F 4/65916* (2013.01)

(58) Field of Classification Search
CPC .................. C07F 17/00; C08F 4/65927; C08F 4/65916; C08F 110/02; C08F 210/16
See application file for complete search history.

(56) References Cited

U.S. PATENT DOCUMENTS

| | | |
|---|---|---|
| 6,342,622 B1 | 1/2002 | Arts et al. |
| 2016/0208025 A1 | 7/2016 | Sankaran et al. |

FOREIGN PATENT DOCUMENTS

| | | |
|---|---|---|
| WO | 9411406 A1 | 5/1994 |
| WO | 2013091836 A1 | 6/2013 |
| WO | 2013091837 A1 | 6/2013 |

OTHER PUBLICATIONS

International Search Report for PCT/EP2014/068353 dated Nov. 24, 2014, 4 pages.
Wang, Huadong et al. "A 1,8-Naphthylene-Bridged Bis(indenyl)zinc THF Adduct: Formation and Structure of an ansa-Zincocene Derivative", Angewandte Chemie International Edition 46(26):4905-4908, Jun. 2007.
Written Opinion of the International Searching Authority for PCT/EP2014/068353 dated Nov. 24, 2014, 6 pages.

*Primary Examiner* — Caixia Lu
(74) *Attorney, Agent, or Firm* — Cantor Colburn LLP

(57) ABSTRACT

The invention relates to a metallocene complex according to formula (1) wherein M is a metal selected from lanthanides or transition metals from group 3, 4, 5 or 6 of the Periodic System of the Elements, Q is an anionic ligand to M, k is the number of Q groups and equals the valence of M minus 2, $Z_1$, $Z_2$, $Z_3$ and $Z_4$ are identical or different and can be chosen from the group consisting of hydrogen and a hydrocarbon radical with 1-20 carbon atoms, and adjacent substituents Z can form a ring system together with the carbon atoms of the Cp ring to which they are bound.

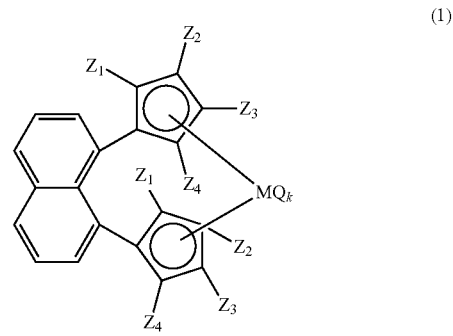

16 Claims, No Drawings

BRIDGED METALLOCENE COMPLEX FOR OLEFIN POLYMERIZATION

This application is a continuation of U.S. patent application Ser. No. 14/912,631 filed on Feb. 18, 2016, which is a national stage application of PCT/EP2014/068353 file on Aug. 29, 2014, which claims priority to European Application EP13182308.0 filed on Aug. 30, 2013, and U.S. Provisional Application 61/929,650 filed on Jan. 21, 2014, and all the benefits accruing therefrom under Title 35 of the United States Code, the contents of all of the above applications being incorporated herein in their entireties by reference.

The invention relates to a metallocene complex, a ligand precursor, a composition comprising the metallocene complex, a process for the production of the ligand precursor, a process for the production of a metallocene complex, a process for the preparation of olefin polymers by polymerizing one or more olefins in the presence of the metallocene complex or the composition and to polyolefin, preferably polyethylene.

The discovery of the organometallic catalyst systems for highly active and stereoselective olefin polymerization by Ziegler and Natta in the 1950s set the stage for rapid progress in polyolefin science and technology. The fact that polyolefin industries, mainly polyethylene (PE) and polypropylene (PP), are fast growing and are set to displace some of the current commercial plastics is largely due to two major reasons: the structure of the polymer and its physical properties and the development of newer catalysts that helps to tune the structure and properties of the polymers to customer needs. PE are of different types. (1) Low density PE (LDPE) with density falling in the range of 0.91-0.94 gcm$^{-3}$ (2) Linear low density PE (LLDPE) having density in the range of 0.915-0.925 gcm$^{-3}$ and produced by the copolymerization of ethylene with short α-olefins such as 1-butene, 1-hexene and 1-octene (3) High density PE (HDPE) with density typically in the range 0.94-0.97 g/cm$^3$.

Metallocene catalysts have only one type of active site and produces polymers with a narrow molar mass distribution. Using metallocene catalysts, the structure of the polymers can be easily tuned. There are various types of catalysts available in literature such as unbridged metallocenes, bridged metallocenes, constrained geometry catalysts, post-metallocenes etc for the polymerization of ethylene. However, it is desirable to develop new catalysts for producing the desired grades of LLDPE.

Bridged metallocene complexes are known in the state of the art and are for instance described in WO94/11406A1 and in U.S. Pat. No. 6,342,622. In these two patent publications metallocene complexes are described comprising two cyclopentadienyl or indenyl ligands that are bridged with a bridging group comprising sp3 or sp2 hybridized carbon atoms. Many of these metallocenes show prolonged polymerization performance over time. This creates the disadvantage, that large polymerization reactors are needed to create enough residence time to achieve sufficient yields of polymer per unit of catalyst. There is a need for catalysts that show high activity in a short amount of time in order to build more efficient polymerization plants and reduce production costs of polyolefins.

Angew. Chem. Int. Ed. 2007, 46, 4905-4908 describes a 1,8-naphthalene-bridged bis (indenyl) ZrCl$_2$ complex. Initial ethylene homo-polymerization experiments have been described for this catalyst. An activity of 1 kg PE (mmol Zr$^{-1}$ h$^{-1}$ bar$^{-1}$) is reported. WO2013/091836 and WO2013/091837 describe bridged bis (indenyl) metallocene complexes eg. 2,2' bis (2-indenyl) biphenyl ZrCl$_2$ and 1,2 bis (2-indenyl) benzene ZrCl$_2$. The results describe the ethylene homopolymerization produced by the 2,2' bis (2-indenyl) biphenyl ZrCl$_2$ and 1,2 bis (2-Indenyl) benzene ZrCl$_2$ with an activity of 225000 and 95060 kg PE/mol Cat.h respectively.

A new family of bridged metallocene complexes has now been discovered which advantageously can be used for olefin polymerization, preferably for ethylene polymerization, and for the copolymerization of ethylene with another olefin. It has been surprisingly discovered that the kinetic profile of polymerization or co-polymerization of ethylene can be modified when these metallocene complexes were used. Additionally, by changing the metal in the metallocene complex, it is believed that the copolymerization of ethylene with other α-olefins will result in ethylene copolymers having desired low densities. Additionally, the complexes may show improved catalytic activity towards ethylene and/or α-olefins polymerization.

Metallocene Complex

The invention relates to a metallocene complex according to formula (1)

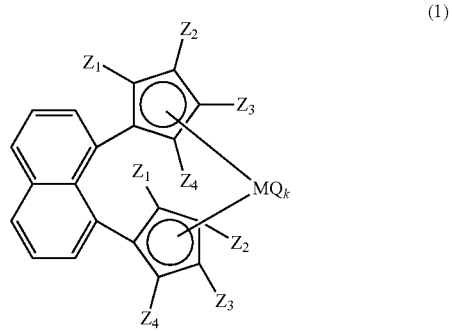

(1)

wherein
M is a metal selected from the group consisting of lanthanides or transition metals from group 3, 4, 5 or 6 of the Periodic System of the Elements,
Q is an anionic ligand to M,
k is the number of Q groups and equals the valence of M minus 2,
$Z_1$, $Z_2$, $Z_3$ and $Z_4$ are identical or different and can be chosen from the group consisting of hydrogen and a hydrocarbon radical with 1-20 carbon atoms, and adjacent substituents Z can form a ring system together with the carbon atoms of the Cp ring to which they are bound, and wherein the metallocene complex is optionally immobilized on a support, with the exception of an unsupported 1,8-naphthalene-bridged bis (indenyl) Zr Cl$_2$ complex as described in Angew. Chem. Int. Ed. 2007, 46, 4905-4908.

The metallocene complex according to the invention comprises a metal selected from lanthanides or transition metals from group 3, 4, 5 or 6 of the Periodic System of the Elements. The Periodic System of the Elements is understood to be the Periodic System of the Elements that can be found at www.chemicool.com. The metal M is preferably chosen from the group consisting of Ti, Zr, Hf, V and Sm, more preferably from Ti, Zr and Hf, most preferably the metal is Zr.

$Z_1$, $Z_2$, $Z_3$ and $Z_4$ are identical or different and can be chosen from the group of hydrogen and a hydrocarbon radical with 1-20 carbon atoms, and adjacent substituents Z can form a ring system together with the carbon atoms of the Cp ring to which they are bound. Hydrocarbon radicals can be alkyl, aryl or aryl alkyl substituents. Examples of alkyl groups are methyl, ethyl, propyl, butyl, hexyl and decyl. Examples of aryl groups are phenyl, mesityl, tolyl, and cumenyl. Examples of aryl alkyl substituents are benzyl, pentamethylbenzyl, xylyl, styryl and trityl. In an embodiment of the invention, two adjacent hydrocarbon radicals may be connected with each other in a ring system. In this way an indenyl group or tetrahydroindenyl group can be formed by connection of $Z_1$ and $Z_2$, $Z_2$ and $Z_3$ and $Z_3$ and $Z_4$, or fluorenyl can be formed by connection of both $Z_1$ and $Z_2$ and $Z_3$ and $Z_4$. Preferably, $Z_1$ and $Z_2$ or $Z_3$ and $Z_4$ are connected and form together a ring system, such that an indenyl or tetrahydroindenyl ligand is formed. Preferably $Z_1$ and $Z_4$ are hydrogen and $Z_2$ and $Z_3$ are connected to form 6 membered ring such as phenyl, substituted phenyls, hydrogenated phenyls or substituted hydrogenated phenyls, wherein preferred substitutions are alkyl groups.

Most preferably $Z_1$ and $Z_4$ are hydrogen and $Z_2$ and $Z_3$ are connected, such that a 2-indenyl ligand or a 2-tetrahydroindenyl ligand is formed.

Q is an anionic ligand to M. The Q ligands preferably are the same and are preferably selected from the group consisting of halogen (F, Cl, Br, I) and hydrocarbyl groups comprising 1 to 20 carbon atoms. More preferably the Q ligands are Cl or a methyl group. k is the number of Q groups and equals the valence of M minus 2; k is an integer.

Preferably, k is 2.

In a preferred embodiment, the invention relates to a metallocene complex according to formula 1a,

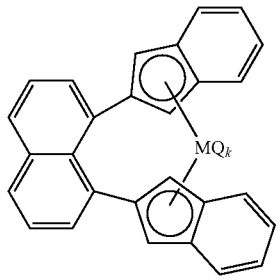

(1a)

wherein M is chosen from the group consisting of lanthanides or transition metals from group 3, 4, 5 or 6 of the Periodic System of the Elements; Q is an anionic ligand to M; k is the number of Q groups and equals the valence of M minus 2, and wherein the metallocene complex is optionally immobilized on a support, with the exception of an unsupported 1,8-naphthalene-bridged bis (indenyl) Zr $Cl_2$ complex as for example described in Angew. Chem. Int. Ed. 2007, 46, 4905-4908.

The metal M is preferably chosen from the group consisting of Ti, Zr, Hf, V and Sm, more preferably from Ti, Zr and Hf, most preferably the metal is Zr or Hf.

Q is an anionic ligand to M. The Q ligands preferably are the same and are preferably selected from the group consisting of halogen (F, Cl, Br, I) and hydrocarbyl groups comprising 1 to 20 carbon atoms. More preferably the Q ligands are Cl or a methyl group. k is the number of Q groups and equals the valence of M minus 2; k is an integer.

Preferably, k is 2.

Support

The metallocene complex according to formula 1 (a) can be present on a support. The support is preferably an inert support, more preferably a porous inert support. Examples of porous inert supports materials are talc and inorganic oxides. Preferably, the support material is in a finely divided form.

Therefore, the invention also relates to a composition comprising the metallocene complex of the invention, wherein the metallocene complex is present on a support.

Suitable inorganic oxide materials include group 2A, 3A, 4A and 4B metal oxides such as silica, alumina and mixtures thereof. Other inorganic oxides that may be employed either alone or in combination with the silica or alumina are magnesia, titania, zirconia and the like. Other support materials, however, can be employed, for example finely divided functionalized polyolefins such as finely divided polyethylene.

Preferably, the support is a silica having a surface area between 200 and 900 $m^2$/g and a pore volume between 0.5 and 4 ml/g.

In order to prepare a metallocene on a support, known techniques can be used. For example the metallocene complex can be dissolved in toluene and mixed with methylaluminoxane, whereby an activated catalyst is being formed. The solution of the activated catalyst is mixed with dry silica. The mixture is dried using vacuum to afford the supported catalyst.

Process

The invention is also related to a method to prepare the ligand precursor according to formula (2).

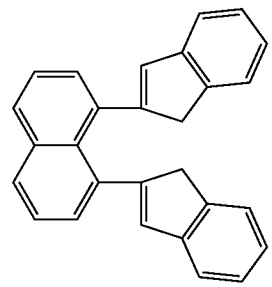

(2)

The process comprises two reaction steps. The ligand precursor (2) can be produced by
a. Reacting 1,8-dibromo-naphtalene with a base and thereafter with trimethyl borate to yield 1,8-naphthalene diboronic acid,
b. Reacting 1,8-naphthalene diboronic acid with 2-bromoindene in the presence of a Pd complex and a Lewis base to arrive at the ligand precursor (2).

Alternatively the ligand precursor (2) can be made by the reaction of 1,8-substituted naphthalene derivatives (for example=Br, OTf, OTs etc.) with 2-indene boronic acid in the presence of Pd complex and Lewis base.

A metallocene complex (1a) can be produced by
a. creating anions of the ligand precursor (2) with an organic or inorganic base,
b. reacting the anion of the compound with $(Me_2N)_a MQ_k$, wherein Me is methyl, M is a metal selected from lanthanides or transition metals from group 3, 4, 5 or 6 of the Periodic System of the Elements, Q is an anionic ligand to M, k is the number of Q groups and equals the valence of M minus 2 and a equals the valence of M minus k, to yield a metallocene complex (1a).

Examples of organic and inorganic bases that can be used for creating anions of the ligand precursors are methyllithium, butyllithium, sec-butyllithium, t-butyllithium, lithiumdiisopropylamide (LDA), sodiumhydride, isopropylmagnesiumchloride-lithiumchloride, s-butylmagnesiumchloride, sodiumhexamethyldisilazide, potassiumhexamethyldisilazide and combinations thereof.

In another aspect, the invention relates to a process for the preparation of olefin polymers by polymerizing one or more olefins in the presence of the metallocene complex of the invention or in the presence of the composition of the invention, wherein the metallocene complex is present on a support and a cocatalyst The cocatalyst employed according to the present invention include aluminium- or boron-containing cocatalysts. Suitable aluminium-containing cocatalysts comprise aluminoxanes and alkyl aluminium. The aluminoxanes usable according to the present invention are well known an preferably comprise oligomeric linear and/or cyclic alkyl aluminoxanes represented by the formula: $R^3\text{-}(AlR^3\text{—}O)_n\text{-}AlR^3{}_2$ for oligomeric, linear aluminoxanes and $(\text{-}AlR^3\text{—}O\text{—})_m$ for oligomeric, cyclic aluminoxanes; wherein n is 1-40, preferably n is 10-20; m is 3-40, preferably m is 3-20 and $R^3$ is a $C_1$ to $C_8$ alkyl group and preferably a methyl group. Further other organoaluminum compounds can be used such as trimethylaluminum, triethylaluminium, triisopropylaluminum, tri-n-propylaluminum, triisobutylaluminum, tri-n-butylaluminum, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride and di-n-butylaluminum hydride.

Suitable boron-containing cocatalysts are trialkylboranes, for example trimethylborane or triethylborane.

In the process to produce olefin polymers by polymerizing one or more olefins in the presence of a metallocene complex preferably an organoaluminum cocatalyst is present. More preferably, methylaluminoxane is used as the cocatalyst.

The process to produce the olefin polymers preferably starts with the reaction of the metallocene complex according to the invention with the cocatalyst. This reaction can be performed in the same vessel as the reaction vessel wherein the olefin polymers are produced or in a separate vessel, whereafter the mixture of the metallocene complex and the cocatalyst is fed to the reaction vessel. During the reaction described above an inert solvent can be used.

In the mixture of the metallocene complex and the cocatalyst, the cocatalyst is used in an amount of 10 to 100,000 mol, preferably from 10 to 10,000 mol per mol of the transition metal compound.

The solvent used in the process to produce olefin polymers may be any organic solvent usually used for the polymerization. Examples of solvents are benzene, toluene, xylene, butane, pentane, hexane, heptane, cyclohexane and methylene chloride. Also the olefin to be polymerized can be used as the solvent.

In the process to produce olefin polymers the polymerization conditions, like for example temperature, time, pressure, monomer concentration can be chosen within wide limits. The polymerization temperature is in the range from −100 to 300° C., preferably 0 to 200° C., more preferably 10 to 100° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, a semi-continuous process or a continuous process and may also be conducted in two or more steps of different polymerization conditions. The polyolefin produced is separated from the polymerization solvent and dried by methods known to a person skilled in the art.

In the process to produce olefin polymers the olefin which is polymerized can be one type of olefin or can be mixtures of different olefins. The polymerization thus includes homopolymerization and copolymerization. Examples of olefins are α-olefins such as ethylene, propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto.

Preferably, at least one of the olefins that is polymerized is ethylene. In one embodiment a mixture of ethylene and at least one other olefin of 3 or more carbon atoms is polymerized. In particular, in the production of LLDPE obtained by copolymerizing ethylene and at least one other olefin of 3 or more carbon atoms a high molecular weight of the olefin polymer can be obtained. Preferably, the other olefin of 3 or more carbon atoms is chosen from 1-butene, 1-hexene or 1-octene, more preferably the other olefin is 1-hexene.

Preferably, the olefin co-monomer is present in an amount of about 5 to about 20 percent by weight of the ethylene-olefin copolymer, more preferably an amount of from about 7 to about 15 percent by weight of the ethylene-alpha olefin copolymer.

For example an LLDPE having a melt mass flow rate (also known as melt flow index) as determined using ASTM D1238-10 (190° C./2.16 kg) which ranges from 1 to 125 g/10 min and a density in the range from 900 kg/m$^3$ to less than 940 kg/m$^3$ as determined using ASTM D1505-10 may be obtained. For example, the density of the linear low density polyethylene ranges from about 0.915 g/cm$^3$ to less than 0.940 g/cm$^3$, for example between 0.915 and 0.925 g/cm$^3$.

Preferably, the density of the polyolefin according to the invention is 0.930-0.940 g/cm$^3$ as determined using ASTM D1505-10 and the bulk density is 0.3 to 0.4.

For example, the melt flow index of the linear low density polyethylene ranges from 0.3 to 3 g/10 min, for example from 0.5 to 1.5 g/10 min.

The production processes of polyethylene are summarised in "Handbook of Polyethylene" by Andrew Peacock (2000; Dekker, ISBN 0824795466) at pages 43-66. The catalysts can be divided in three different subclasses including Ziegler Natta catalysts, Phillips catalysts and single site catalysts. The latter class is a family of different classes of compounds, metallocene catalysts being one of them. As elucidated at pages 53-54 of said Handbook a Ziegler-Natta catalysed polymer is obtained via the interaction of an organometallic compound or hydride of a Group I-III metal with a derivative of a Group IV-VIII transition metal. An example of a (modified) Ziegler-Natta catalyst is a catalyst based on titanium tetra chloride and the organometallic compound triethylaluminium. A difference between metallocene catalysts and Ziegler Natta catalysts is the distribution of active sites. Ziegler Natta catalysts are heterogeneous and have multiple active sites. Consequently polymers produced with these different catalysts will be different regarding for example the molecular weight distribution and the comonomer distribution.

The various processes may be divided into solution polymerisation processes employing homogeneous (soluble) catalysts and processes employing supported (heterogeneous) catalysts. The latter processes include both slurry and gas phase processes.

The invention is also directed to a polyolefin, for example polyethylene, preferably LLDPE obtainable or obtained by the process of the invention, for example by copolymerizing ethylene and at least one other olefin in the presence of a metallocene complex according to the invention or a composition, wherein the metallocene complex according to the invention is present on a support.

As defined herein, in linear low density polyethylene, the term "linear" means that the polymer lacks measurable or demonstrable long chain branches, that is, the polymer is substituted with an average of less than 0.01 long chain branch/1000 carbon atoms. "Long chain branching" (LCB) means a chain length longer than the short chain branch that results from the incorporation of the α-olefin(s) into the polymer backbone. Each long chain branch will have the same comonomer distribution as the polymer backbones and can be as long as the polymer backbone to which it is attached.

As a practical matter, current $^{13}C$ nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example. Zimm, G. H. and Stockmayer, W. H., J. Chem. Phys., 17,1301 (1949) and Rudin. A., Modern Methods of Polymer Characterization, John Wiley & Sons, New York (1991 pp. 103-112).

The amount of incorporation of the at least one other olefin, for example an α-olefin in the polyethylene is expressed by the amount of branches per 1000 carbon atoms.

The presence of short chain branching of up to 6 carbon atoms in length can be determined in ethylene polymers by using $^{13}C$ nuclear magnetic resonance (NMR) spectroscopy and is quantified using the method described by Randall (Rev. Macromol. Chem. Phys., C. 29, V. 2 & 3, p. 285-297).

The number average molecular weight (Mn) of the polyolefin, for example polyethylene, for example LLDPE of the invention may vary between wide ranges and may for example be in the range from 1000 to 200000 g/mol.

For example, the Mn of the polyolefin of the invention may be at least 1500, for example at least 2000, for example at least 20,000, for example at least 50,000 and/or for example at most 150.000, for example at most 110,000, for example at most 100.000, for example at most 70,000.

The weight average molecular weight (Mw) of the polyolefin, for example polyethylene, for example LLDPE of the invention may also vary between wide ranges and may for example be in the range from 1500 to 500000. For example, the Mw of the polyolefin of the invention may be at least 2500, for example at least 10,000, for example at least 50,000, for example at least 100,000 and/or for example at most 400,000, for example at least 350,000, for example at most 300,000, for example at most 250,000.

For purpose of the invention, the Mw and Mn are determined using SEC (Size Exclusion Chromatography) using 1,2,4-trichlorobenzene as an eluent, and calibrated using linear polyethylene standards.

The molecular weight distribution (that is Mw/Mn) of the polyolefin of the invention may for example vary from 2 to 5, from 2.1 to 4 or from 2.5 to 3.5.

The crystallinity temperature (Tc) of the polyolefin of the invention may for example be in the range from 90 to 120° C. The melt temperature (Tm) of the polyolefin of the invention may for example be in the range from 100 to 140° C.

For purpose of the invention, the $T_m$ and $T_c$ are determined using Differential Scanning Calorimetry according to ASTM D 3418-08 using a scan rate of 10'C/min on a sample of 10 mg and using the second heating cycle.

The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight % to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets.

Therefore, in another aspect, the invention also relates to articles comprising the polyolefins obtainable by the process of the invention.

In yet another aspect, the invention also relates to use of the polyolefins obtainable by the process of the invention for the preparation of articles, for example for the preparation of films.

In yet another aspect, the invention relates to a process for the preparation of articles using the polyolefin according to the invention.

Although the invention has been described in detail for purposes of illustration, the skilled man can make variations without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

General remarks relating to the experiments which are performed.

Most of the materials were received from Aldrich. Indene-2-boronic acid was custom synthesized and supplied by Aldrich. The dry solvents used for the reaction were either dried in the lab using standard procedures or obtained from Merck Chemicals India Ltd. 2-bromoindene used in the reactions was procured from TCI, Japan. All materials and reagents used for analysis were of high purity. The reactions were monitored by thin layer chromatograpy (TLC) and High Performance Liquid Chromatography (HPLC). The compounds were purified by different techniques such as by column chromatography, by preparative TLC, by preparative HPLC or by crystallization. The purity of the compounds was analyzed by HPLC. Compounds were characterized by a liquid chromatograph-mass spectrometer (LC-MS) system, comprising a liquid chromatograph and a Quattro Ultima Pt mass spectrometer. An Xterra C18 (50 mm×4.6 mm; 5 microns) column was used for separating the components by liquid chromatography. $^aH$ and $^{13}C$ NMR spectra for all the compounds were recorded on a 300 MHz Bruker NMR spectrometer. CDCl3 was used as the solvent for NMR.

EXAMPLES

Example 1 Synthesis of 1,8-Naphthalene Diboronic Acid

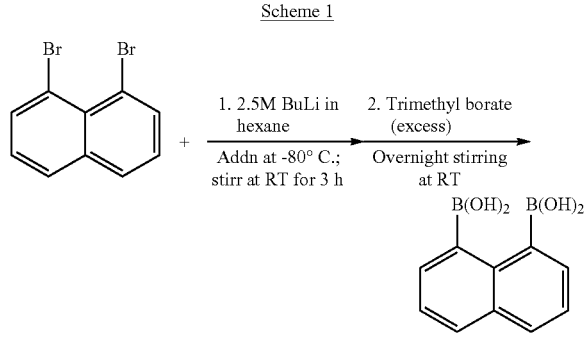

The synthesis of 1,8-naphthalene diboronic acid is shown in scheme 1, above. 1,8-dibromonaphthalene (5 g. 0.0175 moles) was dissolved in diethylether (50 ml) and cooled to −80° C. Butyllithium (2.5M solution in hexane, 21 ml, 0.0525 moles in 50 ml ether) was added dropwise using a dropping funnel. After the addition was completed, the reaction mixture was slowly brought to room temperature. The solution was stirred for 3 hours at room temperature. After this, the reaction mixture was again cooled to −80° C. and trimethyl borate (10 ml, 0.07 moles in 100 ml ether) was added. The reaction mixture was left for stirring at room temperature overnight.

The next day, the reaction was quenched by adding 50 ml of water followed by addition of 100 ml of 2N hydrochloric acid. The mixture was stirred for 45 min and thereafter extracted with ether (3×50 ml). The organic fraction was extracted with 5% sodium hydroxide solution (3×50 ml). The alkaline fraction was acidified with concentrated hydrochloric acid until acidic. A white solid was precipitated. Yield=2.6 g (68%).

Example 2 Synthesis of Bis-2-Indenyl-1,8-Naphthalene

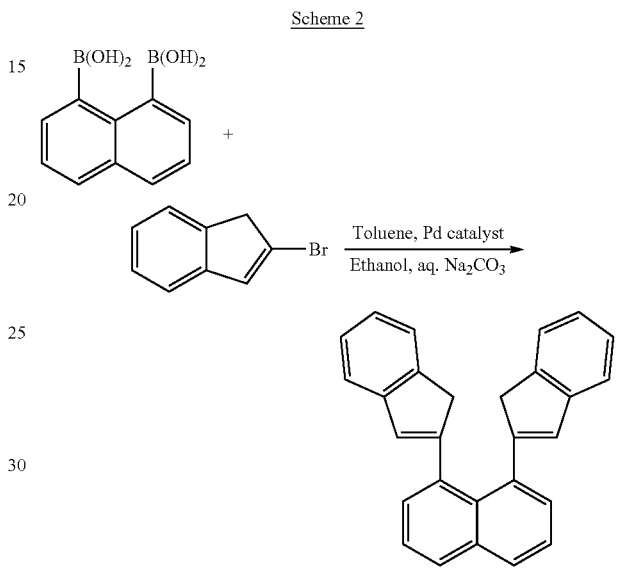

The synthesis of the naphthyl ligand is shown in scheme 2,2-bromoindene (6.66 g, 0.0342 moles) was taken in a round-bottomed flask and dissolved in toluene. Tetrakis triphenyl phosphine palladium (0.054 gm, 8 mol %) was added to the above solution and stirred for 10-15 min. To this solution the diboronic acid from step 1 (3 g. 0.0156 moles) dissolved in ethanol (5 ml) was added, followed by aqueous sodium carbonate (2M, 10 ml). The reaction mixture was heated to 80° C. and stirred for 24 hrs. It was cooled and extracted with dichloromethane (DCM; 5×50 ml). The DCM portion was then extracted with water (2×50 ml), dried over sodium sulfate and concentrated. The crude compound was purified by column chromatography by continuously eluting with hexane as the eluent. Crude yield=3 g; Purified yield=1.6 g (33%)

Alternatively, the below procedure can also be used for the preparation of the ligand precursor.

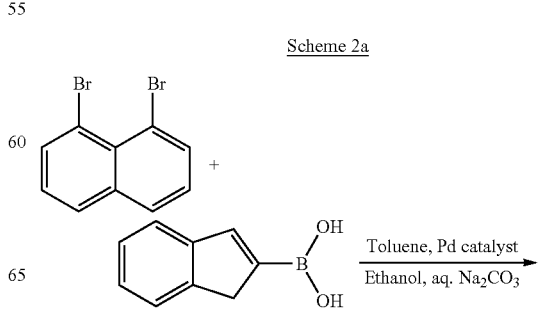

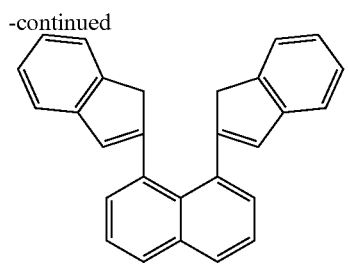

1,8-dibromonaphthalene (5 g, 0.0175 moles) was taken in a round-bottomed flask and dissolved in toluene. Tetrakis triphenyl phosphine palladium (0.1 gm) was added to the above solution and stirred for 10-15 min. To this solution the 2-indene boronic acid (6.71 g, 0.041 moles) dissolved in ethanol (15 ml) was added, followed by aqueous sodium carbonate (2M, 15 ml). The reaction mixture was heated to 80° C. and stirred for 24 hrs. It was cooled and extracted with dichloromethane (DCM; 5×50 ml). The DCM portion was then extracted with water (2×50 ml), dried over sodium sulfate and concentrated. The crude compound was purified by column chromatography by continuously eluting with hexane as the eluent. Yield=30%.

Example 3 Synthesis of 1,8-Naphthalene-Bis(2-Indenyl)ZrCl$_2$

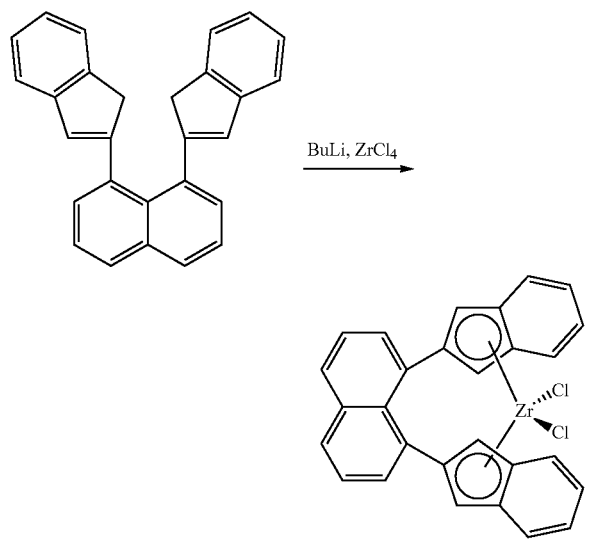

The synthesis of the zirconium complex is shown in scheme 3. The naphthalene ligand was dissolved in tetrahydrofuran (THF, 3.5 g, 0.0098 moles, 70 ml THF). The solution was cooled to −78° C. To the cooled solution butyllithium (BuLi, 7.8 ml (2.5M in hexanes) 0.0196 moles) was added dropwise by using a syringe, very slowly. The solution turned deep red. After the addition of BuLi, stirring was continued for 30 min at −78° C. and then at room temperature for 5 h.

Zirconium chloride (5 gm, 0.0098 moles) was weighed into another round-bottomed flask. The solid was cooled to −78° C. THF (50 ml) and was added dropwise. After the addition, the anion solution was transferred to a dropping funnel fitted to this flask using a cannula. The solution was slowly added to the zirconium chloride solution. After complete addition, the solution was stirred at room temperature overnight and thereafter at 40° C. for 3 h. The solution was then filtered and excess diethyl ether was added. The solution was left in the fridge and filtered cold. The product obtained was recrystallized from toluene. Yield: 1.4 g (28%).

Example 4 Preparing a Metallocene Complex in a Support

The metallocene complex prepared in example 3 was dissolved in toluene and mixed with MAO, 10% in toluene (Al; Zr ratio is 100:1). The solution of the activated catalyst was mixed with 5 g dry silica, Grace 955 (the Zr % is around 0.24). The mixture was dried using vacuum to afford the supported catalyst.

Example 5 Polymerisation

The polymerization experiments were performed by using the polymerization conditions as below. The reactor was a two-liter autoclave vessel, which was heated at 130° C., for 60 minutes under a continuous purge of nitrogen prior to the polymerization reaction. After cooling the autoclave to 85° C., 1 liter of isopentane was introduced into the reactor, and then the reactor was pressurized with 3 bar hydrogen followed by ethylene to pressurize the reactor up to 20 bar. Then 3 ml of triisobutylaluminum (TIBAL)/Amine cocatalyst (1M solution) was injected into the reactor by means of a catalyst injection pump. This was followed by injection of the solid metallocene catalyst (100 mg) in 20 ml of isopentane solvent. The reactor temperature was raised to 88° C. Ethylene polymerization was carried out for 60 minutes; with ethylene supplied continuously to maintain the total reactor pressure at 20 bar. In case a copolymerization experiment is carried out, 100 ml of 1-hexene is introduced into the reactor before pressurizing the reactor with ethylene. In case 1-hexene is used, no hydrogen is fed to the reactor.

Preliminary investigations on the catalytic activity of the supported 1,8-naphthalene-bis(2-indenyl)ZrCl$_2$ catalyst towards ethylene homopolymerization revealed that the catalyst prepared in example 4 produced 4000 gPE/gCat/h as described in Table 1, which is equivalent to 2.07 kgPE/mmol Zr/h. The activity of the naphthalene catalyst towards ethylene polymerization was found to be almost equal to that of a 2,2' bis (2-indenyl) biphenyl ZrCl$_2$ catalyst (4200 gPE/gCat/h) as described in Table 1. It was also observed that the homopolymerization reaction with the naphthalene catalyst was highly exothermic. The catalyst had a high initial activity. This high initial activity makes the catalyst system very suitable for the production of polyethylene in short residence times and smaller polymerization reactors. The activity of the supported catalyst is unexpectedly much higher than the reported activity for the homogeneous catalyst (1 kg PE/mmol Zr/h/bar) as for example described in Angew. Chem. Int. Ed. 2007, 46, 4905-4908.

The catalysts according to the invention are also very suitable for co-polymerization of ethylene with α-olefins. Table 2 describes the ethylene and 1-hexene co-polymerization data. Experiments performed with homogeneous 1,8-naphthalene-bis(2-indenyl)ZrCl$_2$ and 1,8-naphthalene-bis(2-indenyl)HfCl$_2$ show improved co-monomer branching per 1000 C atoms of a LLDPE i.e. around 20% to 40% compared to that of 2,2' bis (2-indenyl) biphenyl ZrCl$_2$ as summarized in Table 2.

The catalysts according to the invention shows an improved MWD with respect to the 2,2' bis (2-indenyl) biphenyl ZrCl₂ as summarized in Table 1. The reduction in the density from 0.9398 g/cm³ produced by 2,2' bis (2-indenyl) biphenyl ZrCl₂ (WO 2013/091836 and WO 2013/091837) to 0.9314 and 0.9335 g/cm³ produced by 1,8-naphthalene-bis(2-indenyl)ZrCl₂ and 1,8-naphthalene-bis(2-indenyl)HfCl₂ respectively indicate that the LLDPE produced from the present invention catalysts will improve its mechanical properties for eg, dart impact, puncture resistance. Moreover, the unsupported 1,8-naphthalene-bis(2-indenyl)ZrCl₂ show higher activity compared to that of unsupported 2,2' bis (2-indenyl) biphenyl ZrCl₂ and 1,8-naphthalene-bis(2-indenyl)ZrCl₂ catalysts.

TABLE 1

Ethylene homopolymerization for supported 1,8-naphthalene-bis(2-indenyl)ZrCl₂ and 2,2' bis (2-indenyl) biphenyl ZrCl₂

| Cat | Activity (kg PE/g cat/hr) |
|---|---|
| 1,8-naphthalene-bis(2-indenyl)ZrCl₂ (Invention) | 4.0 |
| 2,2' bis (2-indenyl) biphenyl ZrCl₂ (Comparison) | 4.2 |

TABLE 2

Ethylene homopolymerization and ethylene-1-hexene copolymerization for unsupported 1,8-naphthalene-bis(2-indenyl)ZrCl₂, 1,8-naphthalene-bis(2-indenyl)HfCl₂ and 2,2' bis (2-indenyl) biphenyl ZrCl₂

| Cat. | Activity (kg PE/g Cat/hr) | GPC | | | DSC | | | Branch per 1000 C atoms | Density (g/cm³) |
| --- | --- | --- | --- | --- | --- | --- | --- | --- | --- |
| | | Mn (g/mol) | MW (g/mol) | MWD | Tm (° C.) | Tc (° C.) | Crystallinity (%) | | |
| 1,8-naphthalene-bis(2-indenyl)ZrCl₂ (Invention) | 86 | 55000 | 162800 | 2.96 | 132 | 114 | 59 | 14.81 | 0.9314 |
| 1,8-naphthalene-bis(2-indenyl)HfCl₂ (Invention) | 16.83 | 94000 | 292500 | 3.11 | 127 | — | 54 | 12.49 | 0.9335 |
| 2,2' bis (2-indenyl) biphenyl ZrCl₂ (Comparison) | 79.92 | 167500 | 381000 | 2.27 | 131 | 117 | 62 | 10.68 | 0.9398 |

The invention claimed is:

1. A composition comprising a metallocene complex according to formula (1b):

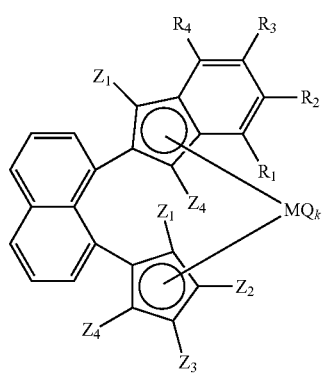

(1b)

wherein

M is a lanthanide metal or a transition metal of Group 3, 4, 5 or 6 of the Periodic System of the Elements, Q is an anionic ligand to M, k is the number of Q groups and equals the valence of M minus 2, $Z_1, Z_2, Z_3, Z_4, R_1, R_2, R_3$ and $R_4$ are identical or different and are hydrogen or a hydrocarbon radical with 1-20 carbon atoms, wherein the metallocene complex is present on a support.

2. The composition according to claim 1, wherein the metallocene complex is according to formula (1b):

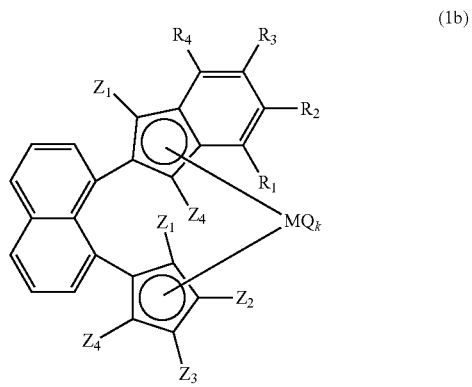

(1b)

wherein

M is Ti, Zr, Hf, V or Sm;

Q is Cl or a methyl group;

k is the number of Q groups and equals the valence of M minus 2; and $Z_1, Z_2, Z_3, Z_4, R_1, R_2, R_3$ and $R_4$ are identical or different and are hydrogen or a hydrocarbon radical with 1-20 carbon atoms.

3. The composition according to claim 1, wherein M is Ti, Zr, Hf, V or Sm.

4. The composition according to claim 1, wherein Q is Cl or a methyl group.

5. A process for the preparation of olefin polymers, comprising polymerizing one or more olefins in the presence of the composition of claim 1.

6. The process according to claim 5, wherein at least one olefin is ethylene.

7. The process according to claim 5, wherein an organoaluminum complex is present.

8. The composition according to claim 1, wherein M is Ti, Zr or Hf.

9. The composition according to claim 1, wherein M is Zr.

10. A process for the preparation of olefin polymers, comprising polymerizing one or more olefins in the presence of the composition according to claim 1 and a cocatalyst.

11. The process according to claim 5, wherein at least one olefin is ethylene.

12. The process according to claim 10, wherein at least one olefin is ethylene.

13. The process according to claim 10, wherein the cocatalyst is an aluminum-containing cocatalyst.

14. A process for the preparation of olefin polymers, comprising polymerizing one or more olefins in the presence of the composition of claim 2 and a cocatalyst.

15. The process according to claim 14, wherein at least one olefin is ethylene.

16. The process according to claim 14, wherein the cocatalyst is an aluminum-containing cocatalyst.

* * * * *